(12) United States Patent
Grözinger et al.

(10) Patent No.: US 7,579,610 B2
(45) Date of Patent: Aug. 25, 2009

(54) EXPANDING, MONITORING, OR ADAPTING A PARTICLE ENERGY DISTRIBUTION OF A THERAPEUTIC PARTICLE BEAM INSTALLATION

(75) Inventors: Sven Oliver Grözinger, Herzogenaurach (DE); Tim Use, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 489 days.

(21) Appl. No.: 11/502,000

(22) Filed: Aug. 9, 2006

(65) Prior Publication Data
US 2007/0034815 A1 Feb. 15, 2007

(30) Foreign Application Priority Data
Aug. 12, 2005 (DE) .................. 10 2005 038 242

(51) Int. Cl.
*H01J 33/00* (2006.01)
(52) U.S. Cl. .................. 250/505.1; 250/492.3
(58) Field of Classification Search .............. 250/505.1, 250/492.3
See application file for complete search history.

(56) References Cited

U.S. PATENT DOCUMENTS

| | | | |
|---|---|---|---|
| 6,891,177 B1 * | 5/2005 | Kraft et al. ............... | 250/505.1 |
| 7,053,389 B2 * | 5/2006 | Yanagisawa et al. ..... | 250/492.3 |
| 2004/0200983 A1 | 10/2004 | Fujimaki et al. | |

FOREIGN PATENT DOCUMENTS

| | | |
|---|---|---|
| EP | 1 378 265 A1 | 1/2004 |
| JP | 07148277 A | 6/1995 |
| JP | 2000084097 A | 3/2000 |
| JP | 2002191709 A | 7/2002 |

OTHER PUBLICATIONS

Y. Futami at al.: "Broad-Beam Three-Dimensional Irradiation System For Heavy-Ion Radiotherapy at HIMAC", *Nuclear Instruments and Methods in Physics Research* A, vol. 430, 1999, pp. 143-153.
B.Schaeffner at al.: "Ridge Filter Design And Optimization For The Broad-Beam Three-Dimensional Irradiation System For Heavy-Ion Radiotherapy," *Med.Phys.*, vol. 27, No. 4, 2000, pp. 716-724.
Weber et al, "Design and Construction of a Ripple Filter for a Smoothed Depth Dose Distribution in Conformal Particle Therapy," *Phys. Med. Biol.* 44 (1999) 2765-2775, pp. 2765-2774.

* cited by examiner

*Primary Examiner*—Kiet T Nguyen
(74) *Attorney, Agent, or Firm*—Brinks Hofer Gilson & Lione

(57) ABSTRACT

A device for expanding a particle energy distribution of a therapeutic particle beam installation and method of producing the same is provided. The device for expanding a particle energy distribution of a therapeutic particle beam installation comprises an expansion element with a structured surface. The expansion element comprises a flexible material. The method for producing an expansion element of a device for expanding a particle beam distribution of a therapeutic particle installation includes forming a negative mold that is a rigid material, filling the negative mold with liquid or jelly material; processing the material into a solid state; and removing the solid state material from the negative mold.

17 Claims, 1 Drawing Sheet

EXPANDING, MONITORING, OR ADAPTING A PARTICLE ENERGY DISTRIBUTION OF A THERAPEUTIC PARTICLE BEAM INSTALLATION

This application claims the benefit of DE 10 2005 038 242.8 filed Aug. 12, 2005, which is hereby incorporated by reference.

FIELD

The present embodiments relate to expanding, monitoring, or adapting a particle energy distribution of a therapeutic particle beam installation.

BACKGROUND

During the course of particle therapy, a patient is generally irradiated with high-energy particles. Particle therapy utilizes an inverse dosage distribution, which has a low dosage of high energy particles at the edges of the particle beam and a high dosage of high energy particles in the area of the maximum penetration range. The maximum penetration range is, for example, the desired area of interaction with the irradiated tissue. Generally, the maximum penetration range is called the Bragg peak, which is a function of the energy of the particles in the particle beam and is set with high accuracy in the direction of the radiation by varying the particle energy distribution.

The width of the Bragg peak is determined by the clarity of the incoming particles. As described in "Design and Construction of a Ripple Filter for a Smoothed Depth Dose Distribution in Conformal Particle Therapy", Phys. Med. Biol. 44 (1999), U. Weber and G. Kraft described on pp. 2765 to 2755, a ripple filter with a raster scanning device has been used in particle therapy to widen the Bragg peak. Other passive devices, which modulate the Bragg peak, have also been used in particle therapy. Devices such as propeller and edge filters, for example, utilize scattering technology and are used to widen the Bragg peak. Propeller and edge filters, for example, either rapidly rotate or rapidly move back and forth in the particle beam to spatially overlap the Bragg maximum. Scattering technology matches the orientation of the Bragg peak with the desired depth of the radiation.

Conventional passive beam-shaping devices, for example, ripple filters, are made of rigid materials, such as PMMA or aluminum. Such materials are formed with high precision and are susceptible to damage when bent or deformed (see the special design of the groove structure in U. Weber and G. Kraft).

It is advantageous if passive beam-shaping elements are guided into and out of an operation position; however, this movement increases the stress on the beam-shaping elements. Thus, the possibility of damage to the beam-shaping element is increased. The installation and removal of the beam-shaping element requires a substantial amount of special area because of the rigid structure of the device. Accordingly, there is a need for a device for expanding, monitoring, or adapting a particle energy distribution of a therapeutic particle radiation distribution that is easily operable, durable, and space efficient.

SUMMARY

The present embodiments are directed to a device for expanding the energy of a particle beam of a therapeutic particle installation, which may obviate one or more of the problems due to the limitations and disadvantages of the related art.

In a present embodiment, a device for expanding a particle energy distribution of a therapeutic particle beam comprises an expansion element with a structured surface. The expansion element comprises a flexible material. In one example embodiment, the flexible material initially comprises of a raw material having tissue-like, moldable and/or water-like properties. For example, it is presently preferred that the density of the material is an order of magnitude of about 1 g/ccm and more preferably is 1.03 g/ccm. In one example embodiment, the flexible material has elastic properties and is easily deformable. In a present embodiment, the material is reversible, for example, the material can be deformed without hysteresis retention. For example, when the expansion element returns to an irradiation position, following a deformed state, the expansion element still has a shape suitable for particle expansion.

The structure of the expansion element can be analytically calculated and optimized to obtain desired expansion properties. For example the surface structure of the expansion element can be modulated. Accordingly, the structure can take any suitable shape. For example, the surface can have a groove structure. Any suitable material can be used to form the expansion element, such as material from RFD Inc. The surface structure is resistant to deformations, so that a desired expansion of the energy distribution is obtained, for example, after an intermediate state has been taken up in the course of the radiation process.

The flexible properties of the expansion element protect against local damage by mechanical effects. In addition, in one embodiment, the expansion element is disposed in a space-efficient manner in an area of the beam outlet. For example, in a first operating position, the expansion element is arranged in an irradiation position for irradiation by the particle beam. In a second operating position, for example, a parked position, the expansion element is disposed outside the particle beam path. The flexibility of the expansion element allows the expansion element to be at least partially deformed during the change from the first operating position to the second operating position, or alternatively, from the second operating position to the first operating position, without the expansion element or its surface structure in particular being damaged. In one example embodiment, the expansion element is rolled up, at least partially, and disposed outside the particle beam path.

In a preferred embodiment of the device, the device has a frame that holds the expansion element and is automatically driven. The device can switch between different operating states by operating the frame. The movement of the frame is not limited to linear movements, for example, movements where no deformation of the expansion element takes place. Alternatively, the frame is operable in a curved motion that is within the bounds of the flexibility of the material.

In one embodiment, the device is arranged between a beam delivery device and a patient. Aside from setting the range, the device for expanding a particle beam distribution may be used in a beam monitoring unit and a beam adaptation unit. For example, a beam monitoring unit monitors the energy distribution and number of particles of the particle beam, and the beam adaptation unit adapts the beam parameters that set the desired energy distribution.

DETAILED DESCRIPTION OF THE PREFERRED EMBODIMENTS

Figure 1:
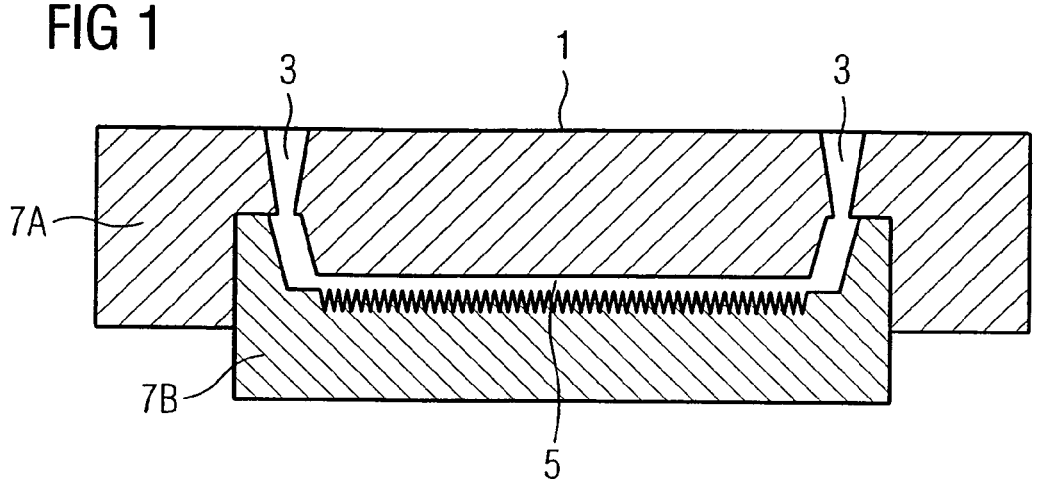
FIG. 1 illustrates a negative mold for producing a device according to an exemplary embodiment.
Figure 2:
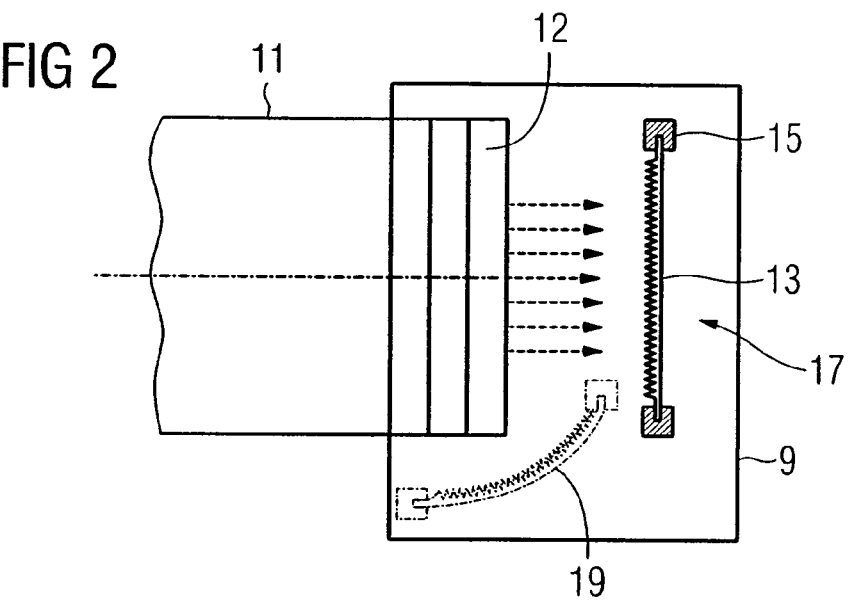
FIG. 2 is a perspective view of a device for expanding a particle beam distribution according to an exemplary embodiment.

FIG. 1 shows a negative mold 1 of an expansion element. The negative mold 1 is a rigid material, for example, steel or aluminum. The negative mold 1 is formed in a highly precise manner, such as in a machining process. The negative mold 1 is divided into an upper element 7A and lower element 7B, so that the expansion element is easily removed. For example, the upper element 7A is removable from the lower element 7B. The negative mold 1 has charging channels 3 through which a liquid or jelly-like raw material reaches a hollow mold chamber 5. In one example embodiment, the inside of the hollow mold chamber 5 is shaped in the manner of a ripple filter.

After a raw material is disposed in the hollow mold chamber 5, the raw material is subjected to a process that causes a change in the aggregate state, for example, from a liquid or jelly-like state to a solid state. Example raw materials include silicon, gel or paraffin. Depending on the material used, this process may vary. For example, the process can take place at different temperatures or pressures as a function of the material properties, such as, but not limited to, degree of linkage.

After the material has hardened, the negative mold 1 is opened. For example, the top element 7A is separated from the lower element 7B. A positive mold, which is, for example, an expansion element, is removed from the negative mold 1. In one exemplary embodiment, the expansion element is flexible. The expansion element demonstrates elastic behavior inside a relevant temperature range and at relevant pressures. In a preferred embodiment, the expansion element has properties equivalent to suitable textiles. The flexibility of the expansion element protects against damage by mechanical effects. Accordingly, the molding process is more efficient than the production of individual passive elements by machining. The elastic material properties allow the expansion element to be deformed when inserted or removed from the particle beam path. In one exemplary embodiment, the insertion of the expansion element into the particle beam is automated. For example, the expansion element is coupled, directly or indirectly, to guide rails that guide the expansion element in a desired radiation position, or alternatively, in a desired storage position on a guide track.

Figure 3:
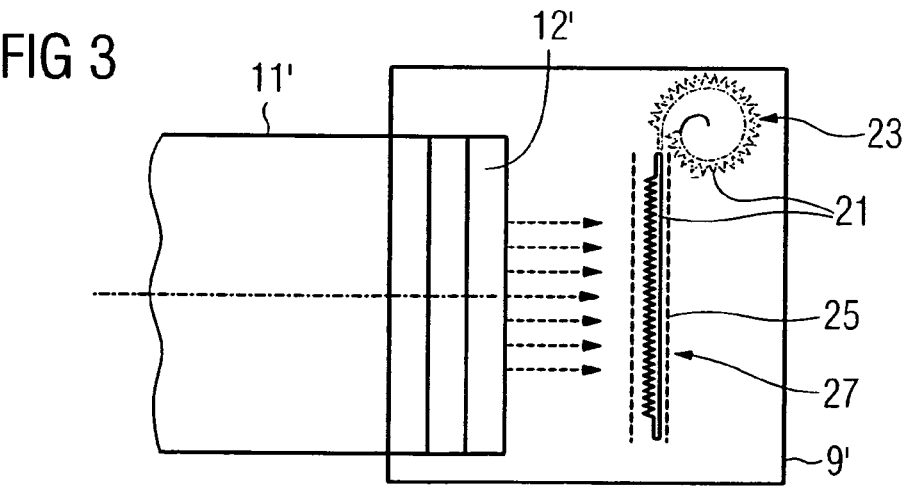
FIG. 3 is a perspective view of a device for expanding a particle beam distribution according to an exemplary embodiment.

As shown in FIG. 3, a beam monitoring unit and a beam adaptation unit of a therapeutic beam therapy installation has a device for expanding a particle energy distribution of a therapeutic particle beam installation.

In a preferred embodiment, as shown in FIGS. 3 and 4, a beam monitoring and beam adaptation unit 9 is provided. The unit 9 follows a beam outlet 11 from an evacuated beam delivery system of a therapeutic particle installation. The unit 9 is the last unit of the therapeutic particle installation and monitors the particle beam with monitoring elements 12. The unit 9 is adapted for its energy distribution properties. For example, when using a raster scanning device, the particle beam exits within a scanning range of, for example, 40 cm×40 cm. As shown in FIG. 3, exemplary positions of the possible beam positions are indicated by dashed arrows.

As shown in FIGS. 3 and 4, in an exemplary embodiment, a device for expanding a particle energy distribution of the particle beam has an expansion element 13, which is held by a frame 15 and spans the particle beam path. In this exemplary embodiment, the expansion element 13 is made of a flexible material.

In one exemplary embodiment, the device for expanding a particle energy distribution has a first operating state. In the first operating state, the expansion element 13 is disposed so a particle beam passes through the expansion element 13. For example, the expansion element 13 is in an irradiation position 17. In a second operating state, when the device is no longer needed, the expansion element 13 is disposed outside the particle beam path, for example, in a parked position. In this exemplary embodiment, the holder or frame 15 moves, for example, on guide rails 25, into a second operating state 19 (drawn in dashed lines). In an alternative embodiment, the expansion element is deformed in a space-saving manner in the second operating state. For example, the expansion element is disposed in a curved parked position next to the beam outlet 11.

As shown in FIG. 4, a beam monitoring or beam adaptation unit 9' having a beam outlet 11' has an expansion element 21 and monitoring elements 12'. In a second operating state, for example, the expansion element 21 is in a rolled-up state (indicated by dashed lines) in a parked position 23 outside of the particle beam path. The expansion element is moved via guide rails 25 out of this parked position into an irradiation position 27.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

What is claimed is:

1. A device for expanding a particle energy distribution of a therapeutic particle beam installation comprising an expansion element with a structured surface, wherein the expansion element comprises a flexible material.

2. The device in accordance with claim 1, wherein the flexible material has a density of approximately 1 g/ccm.

3. The device in accordance with claim 2, wherein at least a portion of the flexible material has properties similar to water with respect to interaction with the particle beam.

4. The device in accordance with claim 1, wherein the flexible material has a density of 1.03 g/ccm.

5. The device in accordance with claim 1, wherein at least a portion of the flexible material has properties similar to water with respect to interaction with the particle beam.

6. The device in accordance with claim 1, wherein the flexible material comprises elastic properties.

7. The device in accordance with claim 6, wherein the flexible material is deformable.

8. The device in accordance with claim 7, wherein the flexible material is free of hysteresis.

9. The device in accordance with claim 1, wherein the flexible material contains silicon, gel or paraffin.

10. The device in accordance with claim 1, further comprising:
- a first operating state for irradiation by the particle beam, the expansion element arranged in an irradiation position; and
- a second operating state in a parked position wherein the expansion element has a deformed state during a change between the first and second operating states.

11. The device in accordance with claim 10, wherein the expansion element is at least partially rolled up in the second operating state.

12. The device in accordance with claim 10, wherein the device has a frame, guide rails, or the combination thereof.

13. The device in accordance with claim 12, wherein the frame holds the expansion element and is displaceable along the guide rails.

14. A beam monitoring unit of a therapeutic beam therapy installation, comprising an expansion element with a structured surface, wherein the expansion element comprises a flexible material.

15. The beam monitoring unit of claim 14 further comprising:
- a first operating state for irradiation by a particle beam, the expansion element arranged in an irradiation position; and
- a second operating state in a parked position wherein the expansion element has a deformed state during a change between the first and second operating states;
- wherein the unit has a frame, guide rails, or the combination thereof; and
- wherein the frame holds the expansion element and is displaceable along the guide rails.

16. A beam adaptation unit of a therapeutic beam therapy installation, comprising an expansion element with a structured surface, wherein the expansion element comprises a flexible material.

17. The beam adaptation unit of claim 16 further comprising:
- a first operating state for irradiation by a particle beam, the expansion element arranged in an irradiation position; and
- a second operating state in a parked position wherein the expansion element has a deformed state during a change between the first and second operating states;
- wherein the unit has a frame, guide rails, or the combination thereof; and
- wherein the frame holds the expansion element and is displaceable along the guide rails.

* * * * *